US007079887B2

(12) United States Patent
Burnes et al.

(10) Patent No.: US 7,079,887 B2
(45) Date of Patent: Jul. 18, 2006

(54) METHOD AND APPARATUS FOR GAUGING CARDIAC STATUS USING POST PREMATURE HEART RATE TURBULENCE (75) Inventors: John E. Burnes, Andover, MN (US); Lawrence J. Mulligan, Andover, MN (US); Michael R. S. Hill, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 351 days.

(21) Appl. No.: 10/394,778

(22) Filed: Mar. 20, 2003

(65) Prior Publication Data

US 2004/0186525 A1    Sep. 23, 2004

(51) Int. Cl.
*A61B 5/04* (2006.01)
(52) U.S. Cl. ..................................... 600/510
(58) Field of Classification Search ............ 600/510; 607/30, 31, 120
See application file for complete search history.

(56) References Cited

U.S. PATENT DOCUMENTS

| 4,506,680 | A | * | 3/1985 | Stokes ......................... 607/120 |
| 4,557,266 | A | * | 12/1985 | Schober ....................... 607/30 |
| 5,213,098 | A | | 5/1993 | Bennett et al. |
| 2002/0120306 | A1 | | 8/2002 | Zhu et al. ..................... 607/25 |

FOREIGN PATENT DOCUMENTS

| EP | 1 197 243 A2 | 4/2002 |
| WO | WO 01/76469 A2 | 10/2001 |

OTHER PUBLICATIONS

Berkowitsch et al., "Normalization of RR Sequences: A New Approach for Quantitative Assessment of Heart Rate Turbulence by Abnormal Post Stimulation Response", *Computers in Cardiology*, 2001; 28:321-324.

Przemyslaw et al., "A Phenomenon of Heart-Rate Turbulence, its Evaluation, and Prognostic Value", *Cardiac Electrophysiology Review*, 2002; 6:256-261.

"Relation of Heart Rate and Blood Pressure Turbulence Following Premature Ventricular Complexes to Baroreflex Sensitivity in Chronic Congestive Heart Failure", Davies, et al., American Journal of Cardiology, Mar. 15, 2001: 87(6):737-42.

"Heart-Rate Turbulence After Ventricular Premature Beats as a Predictor of Mortality After Acute Myocardial Infarction," Schmidt, et al., Lancet, Apr. 24, 1999; 353(9162):1390-6.

(Continued)

*Primary Examiner*—George Manuel
(74) *Attorney, Agent, or Firm*—Paul H. McDowall; Girma Wolde-Michael (57) ABSTRACT A hemodynamic status of a patient is determined in an implanted medical device (IMD) by observing a perturbation of the patient's heart, measuring heart rate turbulence resulting from the perturbation, and quantifying the heart rate turbulence to determine the hemodynamic status. The perturbation may be naturally-occurring, or may be generated by the implantable medical device. The patient's response to heart rate turbulence may also be used to provide a response to the patient, such as providing an alarm and/or administering a therapy. Heart rate turbulence may also be used to tune and/or optimize a device parameter such as A-V or V—V pacing intervals.

40 Claims, 5 Drawing Sheets

OTHER PUBLICATIONS

"Prediction of Major Arrhythmic Events and Sudden Cardiac Death in Dilated Cariomyopathy. The Margurn Cardiomyopathy Study Design and Description of Baseline Clinical Characteristics," Grimm, et al., Herz, May 2000; 25(3): 189-99.

"Blunted Arterial Baroreflex Causes "Pathological" Heart Rate Turbulence," Mrowka, et al., AJP—Regulatory, Integrative and Comparative Physiology, Oct. 2000, vol. 279, Issue 4, R1171-75.

"Postextrasystolic Regulation Patterns of Blood Pressure and Heart Rate in Patients with Idiopathic Dilated Cardiomyopath," The Journal of Physiology, 2002, 538.1, pp. 271-278.

* cited by examiner

METHOD AND APPARATUS FOR GAUGING CARDIAC STATUS USING POST PREMATURE HEART RATE TURBULENCE

FIELD OF INVENTION

The invention relates to cardiac health and, more particularly, to devices and techniques for gauging cardiac and/or hemodynamic status.

BACKGROUND OF INVENTION

Hemodynamics is the study of the physical force generated by the heart to pump blood through the cardiovascular system, including such factors as blood pressure, blood flow and the like. A patient's hemodynamic status is known to be related to the overall health of the cardiovascular system, and a degraded hemodynamic status may be indicative of heart disease, hypertension, and/or other cardiac disorders. Hemodynamic status may also be important in evaluating a patient's pharmacological regimen, pacemaker performance, and/or general health.

Although many techniques of gauging hemodynamic status have existed for some time, these techniques have typically required the patient to consult a health care provider to be effective. Hemodynamic status has traditionally been monitored with a pulmonary artery catheter (PAC), which involves an invasive procedure to place the catheter into the patient. More recently, various non-invasive (or minimally invasive) techniques have become available, including impedance cardiography (ICG), partial $CO_2$ rebreathing, trans-esophageal doppler, and the like. Nevertheless, each of these techniques requires access to specialized equipment that is typically available only at a health care facility. As a result, patients are typically unaware of issues with their hemodynamic status until a major episode occurs and the patient arrives at an emergency room or trauma center.

Accordingly, it is desirable to create a device and/or technique that is capable of gauging hemodynamic status so that any issues can be quickly and appropriately treated. Further, it is desirable to diagnose hemodynamic status within an implantable or other device that can remain with the patient at all times. Moreover, it is desirable to create a technique for optimizing the performance of a pacemaker or other implantable device based upon hemodynamic status. Furthermore, other desirable features and characteristics of the present invention will become apparent from the subsequent detailed description and the appended claims, taken in conjunction with the accompanying drawings and this background of the invention.

BRIEF DESCRIPTION OF EXEMPLARY EMBODIMENTS

According to various exemplary embodiments, hemodynamic status of a patient may be determined in an implanted medical device (IMD) by observing a perturbation of the patient's heart rate, measuring heart rate turbulence resulting from the perturbation, and quantifying the heart rate turbulence to determine the hemodynamic status. The perturbation may be naturally-occurring, or may be generated by the implantable medical device (IMD). The patient's response to heart rate turbulence may also be used to provide a response to the patient, such as providing an alarm and/or administering a therapy. Heart rate turbulence may be further used to tune and/or optimize a pacing parameter such as A-V or V—V pacing intervals.

BRIEF DESCRIPTION OF DRAWINGS

Various exemplary embodiments will hereinafter be described in conjunction with the following drawing figures, wherein like numerals denote like elements, and.

DETAILED DESCRIPTION OF EXEMPLARY EMBODIMENTS

The following detailed description is exemplary in nature and is not intended to limit the invention or the application and uses of the invention. Furthermore, there is no intention to be bound by any theory presented in the preceding background of the invention or the following detailed description of the drawings.

It has recently been discovered that heart rate and blood pressure turbulence resulting from premature ventricular contractions (PVCs), premature atrial contractions (PACs), or other abnormal heartbeats may be indicative of the current baroreflex response, which in turn is an indicator of hemodynamic status and overall cardiac health. When a patient experiences a PVC or other perturbation, the heart typically does not have ample time to fill with blood prior to the premature beat, thus resulting in reduced arterial blood pressure and blood flow. This change in blood pressure typically stimulates baroreceptors, which are nerve endings in the vasculature that are sensitive to changes in blood pressure. When the baroreceptors are stimulated, a neural reflex affects the heart and vasculature to increase heart rate and blood pressure in an attempt to restore the body to its normal state. Until the normal pressure can be restored, however, turbulence is frequently observed in the patient's heart rate due to the changes in cardiac output. If the patient is in good health, the response to changes in cardiac output and arterial pressure is relatively large and the heart recovers relatively quickly. If the patient has poor arterial baroreflexes, however, the magnitude of the turbulence is generally smaller, thereby resulting in heart rate changes over a longer recovery period. Accordingly, the duration and magnitude of heart rate turbulence (HRT) following a heart beat perturbation can be a good indicator of the heart's autonomic tone, as well as the overall hemodynamic status of the patient. In particular, measuring HRT following a heart rate perturbation is believed to be useful in identifying patient's at risk for congestive heart failure (CHF), CHF decompensation, sudden cardiac death, and other forms of heart disease.

The relationship between HRT and cardiac health can be beneficially exploited in an implantable medical device (IMD) such as a pacemaker, implantable cardioverter-defibrillator (ICD), an automatic external defibrillator (AED) or heart monitor and the like. According to various embodiments of the present invention, an implantable medical device (IMD) monitors heart rate turbulence resulting from a heart rate perturbation (e.g., a PVC) to determine an indication of the patient's cardiac health. The perturbation may be naturally occurring in the patient, or may be produced by the IMD or another appropriate device. Turbulence measurements made by the IMD are then used for enhanced monitoring, diagnosis and/or therapeutic functions in response to the measured turbulence. For example, the IMD may store diagnostic data in a memory, activate an alarm to the patient if the episode requires immediate medical attention, or the like. In further embodiments, the IMD administers or adjusts an appropriate therapy or other response when such treatment or adjustment to the treatment is warranted. As used herein, the term "response" is intended to broadly encompass any type of medical response, alarm, report, telemetered data or the like (including storage of data within the IMD), as well as any of the various therapies that may be provided by the IMD to the patient. In a further embodiment, HRT may be used to determine optimal settings for a pacemaker, or for optimal delivery of a pharmaceutical or other therapy. In practice, HRT can be effectively manipulated and monitored by mechanisms present in many conventional IMDs, thus making HRT a very effective parameter for monitoring or improving a patient's cardiac health.

Figure 1:
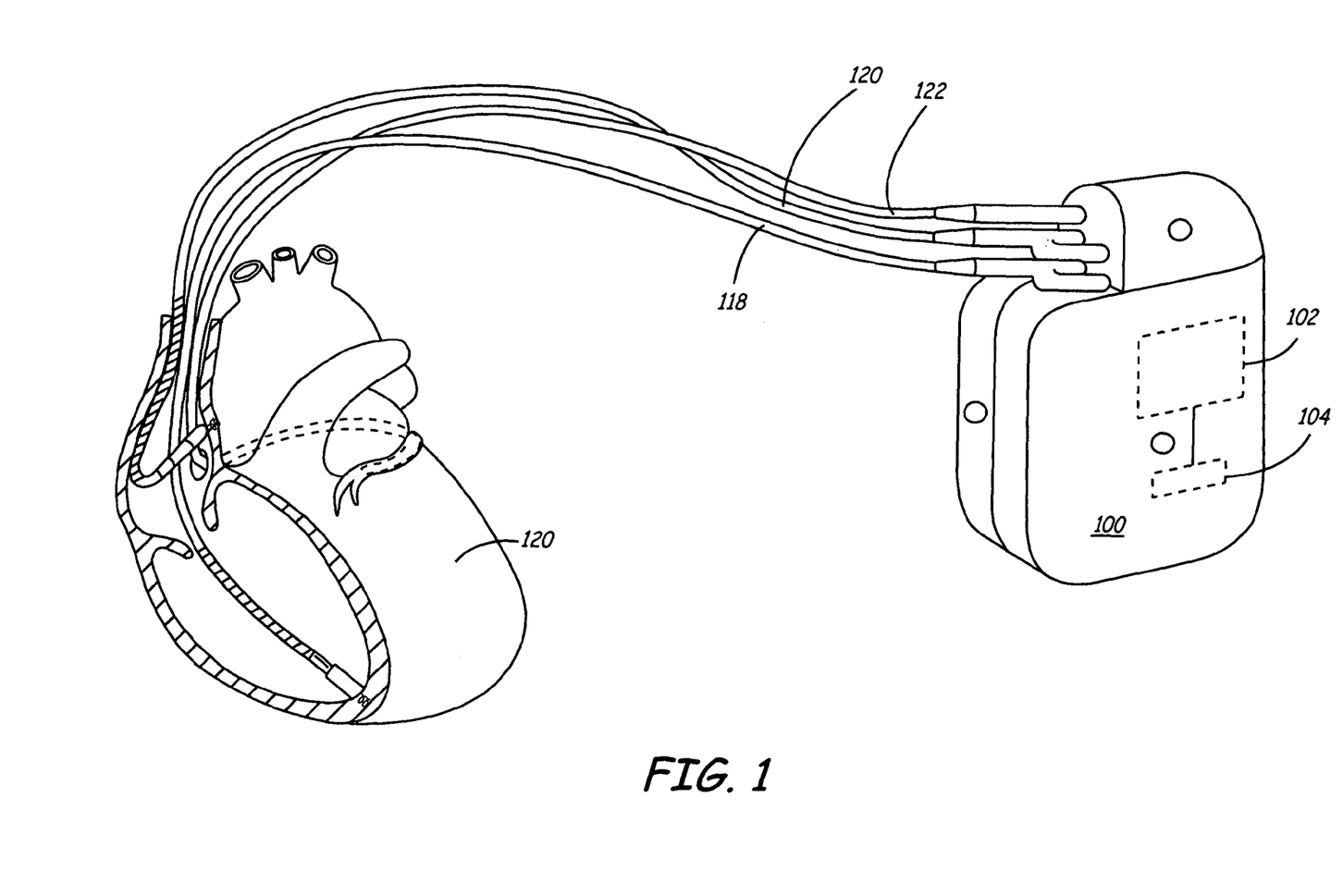
FIG. 1 is a diagram illustrating an exemplary implantable medical device in association with a patient's heart.

With reference now to FIG. 1, an exemplary implantable medical device (IMD) 100 is connected to monitor a patient's heart 120. IMD 100 may be further configured to integrate both monitoring and therapy features, as will be described below. IMD 100 suitably collects and processes data about heart 120 from one or more sources (e.g. heart rate monitor, blood pressure monitor, electrocardiogram (ECG) waveform, electrogram (EGM) waveform, or more generally PQRST waveform, or portion of such waveform, etc.). IMD 100 may further provide therapy or other response to the patient as appropriate, and as described more fully below. As shown in FIG. 1, IMD 100 may be generally flat and thin to permit subcutaneous implantation within a human body, e.g., within upper thoracic regions or the lower abdominal region. IMD 100 may include a hermetically-sealed housing that encloses a processor 102, a digital memory 104, and other components as appropriate to produce the desired functionalities of the device. In various embodiments, IMD 100 is implemented as any implanted medical device capable of measuring the heart rate of a patient, including, but not limited to a pacemaker, defibrillator, electrocardiogram monitor, blood pressure monitor, drug pump, insulin monitor, or neurostimulator.

Processor 102 may be implemented with any type of microprocessor, digital signal processor, application specific integrated circuit (ASIC), field programmable gate array (FPGA) or other integrated or discrete logic circuitry programmed or otherwise configured to provide functionality as described herein. Processor 102 executes instructions stored in digital memory 104 to provide functionality as described below. Instructions provided to processor 102 may be executed in any manner, using any data structures, architecture, programming language and/or other techniques. Digital memory 104 is any storage medium capable of maintaining digital data and instructions provided to processor 102 such as a static or dynamic random access memory (RAM), or any other electronic, magnetic, optical or other storage medium.

As further shown in FIG. 1, IMD 100 may receive one or more cardiac leads for connection to circuitry enclosed within the housing. In the example of FIG. 1, IMD 100 receives a right ventricular endocardial lead 118, a left ventricular coronary sinus endocardial 122, and a right atrial endocardial lead 120, although the particular cardiac leads used will vary widely from embodiment to embodiment. In addition, the housing of IMD 100 may function as an electrode, along with other electrodes that may be provided at various locations on the housing of IMD 100. In alternate embodiments, other data inputs, leads, electrodes and the like may be provided. Ventricular leads 118 and 122 may include, for example, pacing electrodes and defibrillation coil electrodes (not shown) in the event IMD 100 is configured to provide pacing, cardioversion and/or defibrillation. In addition, ventricular leads 118 and 122 may deliver pacing stimuli in a coordinated fashion to provide biventricular pacing, cardiac resynchronization or other benefits. IMD 100 may also obtain input data from other internal or external sources (not shown) such as a blood pressure monitor, pH monitor, accelerometer or the like.

In operation, IMD 100 suitably obtains data about heart 120 via leads 118, 120, 122, and/or other sources. This data is provided to processor 102, which suitably analyzes the data, stores appropriate data about the episode in memory 104, and/or provides a response or report as appropriate. Any identified cardiac episodes (e.g. an arrhythmia or heart failure decompensation) can be treated by intervention of a physician or in an automated manner. In various embodiments, IMD 100 activates an alarm upon detection of a cardiac episode. Alternatively or in addition to alarm activation, IMD 100 selects or adjusts a therapy and coordinates the delivery of the therapy by IMD 100 or another appropriate device. Optional therapies that may be applied in various embodiments may include drug delivery, electrical stimulation, neurostimulation, modifications in pacing rate, and/or the like.

Figure 2:
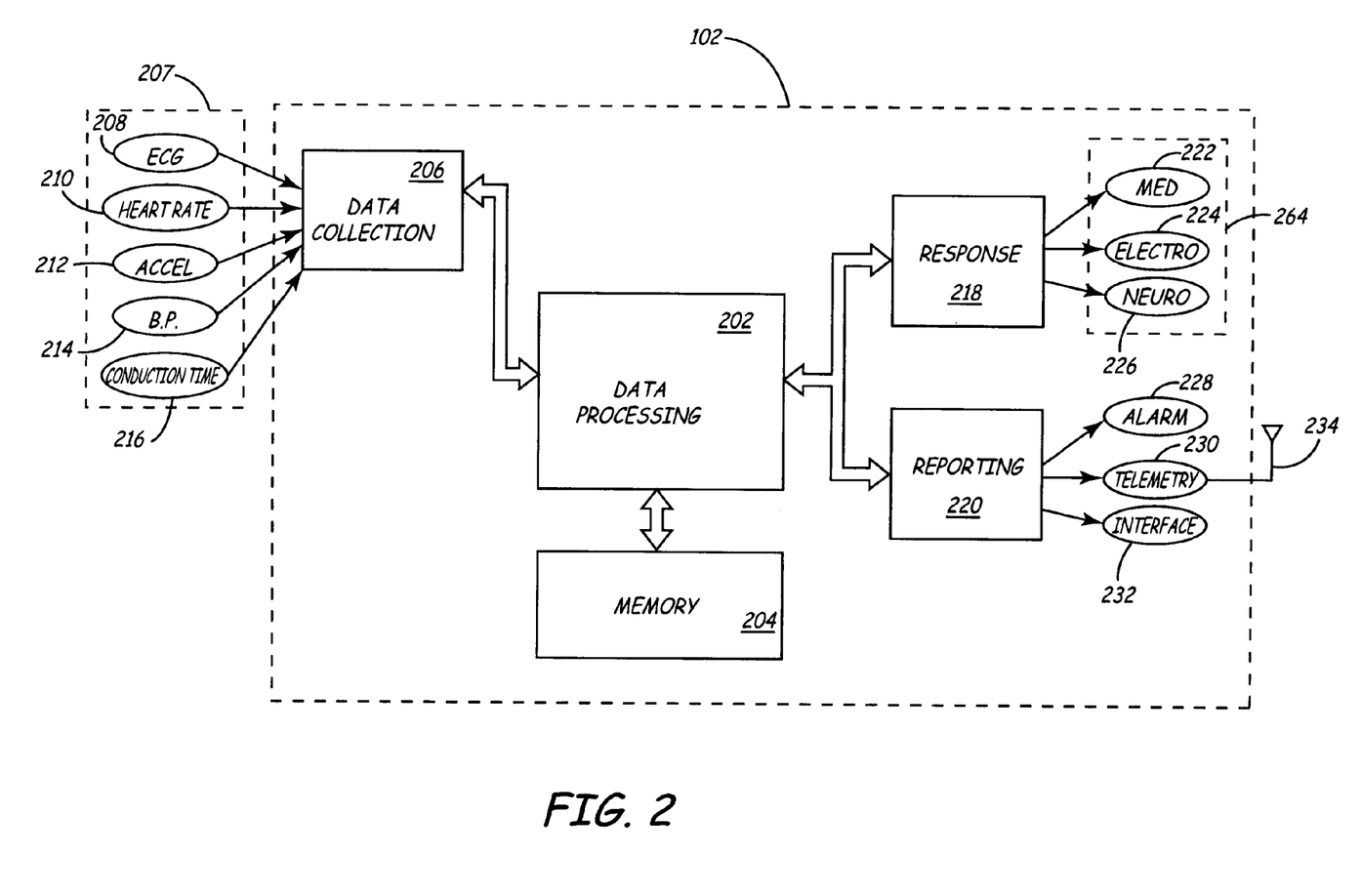
FIG. 2 is a conceptual block diagram showing exemplary processing modules for an implantable medical device.

With reference now to FIG. 2, an exemplary data processing layout for an IMD 100 suitably includes a data collection module 206, a data processing module 202, a response module 218 and/or a reporting module 220. Each of the various modules may be implemented with computer-executable instructions stored in memory 104 and executing on processor 102 (FIG. 1), or in any other manner. The exemplary modules and blocks shown in FIG. 2 are intended to illustrate one logical model for implementing an IMD 100, and should not be construed as limiting. Indeed, the various practical embodiments may have widely varying software modules, data structures, applications, processes and the like. As such, the various functions of each module may in practice be combined, augmented, optimized or otherwise differently-organized in any fashion.

Data collection module 206 suitably interacts with one or more data sources 207 to obtain data about the patient. Data sources 207 include any source of information about the patient's heart, blood, temperature or the like. In various embodiments, data sources 207 include an ECG or EGM source 208 that provides electrical impulses or other observed signals that can be used to model the patient's electrocardiogram (ECG) waveform. Other data sources 207 may include a heart rate sensor 210, a blood pressure monitor 214, an accelerometer 212, a sensor 216 for determining cardiac conduction time and/or the like. The various data sources 207 may be provided alone or in any combination with each other, and may vary widely from embodiment to embodiment. Sensors for cardiac conduction time 216 and heart waveform 208 data could be combined into a single pair of electrodes, for example. Moreover, other data sources 207 such as temperature sensors, blood pH sensors or the like could additionally or alternatively be provided.

Data collection module 206 suitably receives data from each of the data sources 207 by polling each of the sources 207, by responding to interrupts or other signals generated by the sources 207, by receiving data at regular time intervals, or according to any other temporal scheme. Data may be received at data collection module 206 in digital or analog format according to any protocol. If any of the data sources generate analog data, data collection module 206 suitably translates the analog signals to digital equivalents using any form of analog-to-digital conversion scheme presently known or subsequently developed. Data collection module may also convert data from protocols used by data sources 207 to data formats acceptable to data processing module 202, as appropriate.

Data processing module 202 is any circuit, programming routine, application or other hardware/software module that is capable of processing data received from data collection module 206. In various embodiments, data processing module 202 is a software application executing on processor 102 (FIG. 1) to implement the process described below in conjunction with FIG. 3. Accordingly, data processing module 202 suitably interprets received cardiac electrophysiologic or other data to quantify heart rate turbulence in the patient and to produce an appropriate response, as described more fully below.

Issues in the patient's cardiac health can be detected, for example, when the patient's HRT deviates from a baseline reading by more than a threshold amount, when the patient's cardiac conduction time exceeds a threshold value, or according to any other criteria. The baseline HRT may be a static value, or may be updated over time. In various embodiments, the baseline data represents a mean or median HRT value observed over any appropriate number of preceding samples. Threshold values may be any nominal values derived from a typical implanted cardioverter-defibrillator device (ICD) population of patients, or from any other source. Alternatively, the threshold values may be independently adjusted and set for a given patient as desired by the attending physician. In various embodiments, the more recent values of HRT, as well as other information, may be stored in a memory 204 to facilitate diagnosis of the patient. In another embodiment, HRT values during a time period or near a cardiac event deemed important by algorithms in the IMD (e.g. preceding an observed arrhythmia) may be stored in a memory 204 to facilitate diagnosis of the patient.

In an exemplary embodiment, processing module 202 receives ECG or EGM waveform data 208 and/or other appropriate information from data collection module 206 and interprets the data using conventional digital signal processing techniques. If a heart beat perturbation occurs, data about the episode (e.g. the duration and magnitude of HRT, time and date of the episode, and/or the like) may be stored in memory 204, which may correspond to hardware memory 104 shown in FIG. 1, or may be implemented with any other available digital storage device.

When a perturbation is identified, processing module 202 may trigger an appropriate response if warranted by the HRT resulting from the perturbation. Responses may be activated by sending a digital message in the form of a signal, passed parameter or the like to response module 218 and/or reporting module 220.

Reporting module 220 is any circuit or routine capable of producing appropriate feedback from the IMD to the patient or to a physician. In various embodiments, suitable reports might include storing data in memory 204, generating an audible, tactile, and/or visible alarm 228, producing a wireless message transmitted from a telemetry circuit 230 via an antenna 234, or providing other data that may be downloaded from a serial, parallel or other interface 232. Reports may include information about the duration, frequency and/or amplitudes of HRT observed, time and date of episode occurrence, or any other appropriate data. In a further embodiment, the particular response provided by reporting module 220 may vary depending upon the severity of the episode. Minor episodes may result in no alarm at all, for example, or a relatively non-obtrusive visual, tactile and/or audible alarm. More severe episodes might result in a more noticeable alarm, in addition to an automatic response as described below.

Telemetry circuitry 230 communicates data from IMD 100 to an external device via antenna 234. The external device receiving the wireless message may be a programmer/output device that advises the patient, a physician or other attendant of serious conditions, e.g., via a display or a visible or audible alarm. Information stored in memory 204 may be provided to an external device via antenna 234 for example, to aid in diagnosis or treatment of the patient. Alternatively, the external device may be an interface to a telephone network such that IMD 100 is able to automatically notify emergency personnel if an extreme episode occurs.

Interface 232 is any serial, parallel or other interface to an external computing device. Interface 232 and/or telemetry circuit 230 may be used to provide information from IMD 100 to an external device. Information stored in memory 204 may be provided to an external digital computer or other device, for example, to aid in diagnosis or treatment of the patient.

Response module 218 is any circuit, software application or other component that interacts with any type of therapy-providing system 264, which may include any type of therapy deliver mechanisms such as a drug delivery system 222, neurostimulation 226 and/or cardiac stimulation 224. In some embodiments, response module 218 may alternatively or additionally interact with an electrical stimulation therapy device integrated with IMD 100 to deliver pacing, post-extrasystolic potentiation (PESP), cardioversion, defibrillation and/or any other therapy. The following two patent disclosures relating to PESP are hereby incorporated by reference herein; namely: U.S. Pat. No. 5,213,098 and non-provisional U.S. patent application Ser. No. 10/232,792 filed 28 Aug. 2002. Accordingly, the various responses to HRT that may be provided by IMD 100 vary from simple storage of data to actual provision of therapy in various embodiments. Any therapy provided may be titrated or otherwise adjusted in response to HRT observed, as described more fully below. Drug dosage may be adjusted according to episode severity, for example, or pacing parameters can be adjusted in response to observed HRT.

The various components and processing modules of IMD 100 may be housed in a common housing such as that shown in FIG. 1. Alternatively, portions of IMD 100 may be housed separately. For example, portions of the therapy delivery system 264 could be integrated with IMD 100 or provided in a separate housing, particularly where the therapy delivery system includes drug delivery capabilities. In this case, response module 218 may interact with therapy delivery system 264 via an electrical cable or wireless link, or via interface 232.

Figure 3:
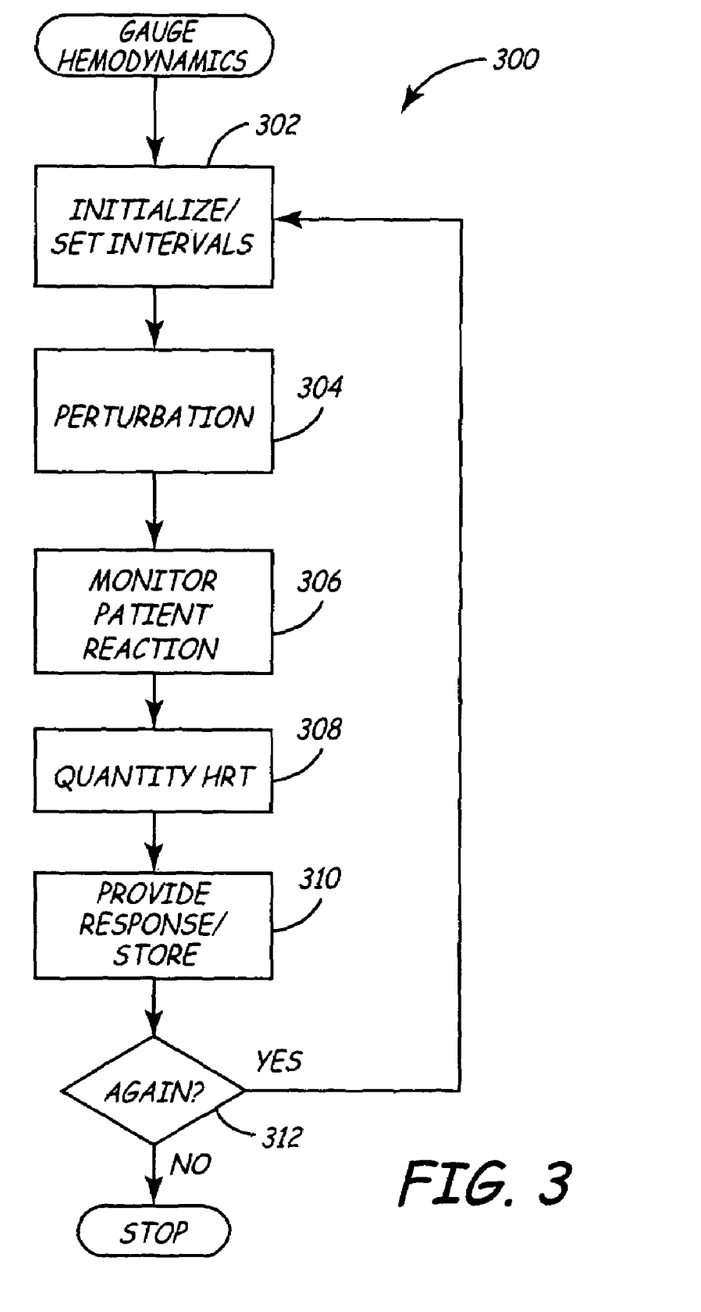
FIG. 3 is a flowchart of an exemplary process for gauging a patient's hemodynamics that may be executed within an implantable medical device.

With reference now to FIG. 3, an exemplary process 300 for gauging the hemodynamic status of a patient suitably includes the broad steps of generating and/or observing a heart rate perturbation (step 304), measuring the associated heart rate turbulence generated by the perturbation (step 306), and processing or quantifying the data to correlate the heart rate turbulence with the patient's hemodynamic status and/or cardiac health (step 308). In various embodiments, the various steps of process 300 may be implemented with computer-executable instructions that are stored in a digital memory 104 and that are appropriately executed by processor 102 (FIG. 1), or by any other processor associated with the IMD.

Process 300 suitably begins by setting appropriate pacing intervals by IMD 302 and/or otherwise initializing the IMD for the gauging process (step 302). An exemplary technique for determining optimum pacing intervals is set forth below in conjunction with FIG. 5, although any steady state pacing routine could be used in alternate embodiments. Initialization may also include setting or resetting any counters, timers or other variables within processor 102 as appropriate. After pacing intervals are set, it may be desirable to maintain the pacing state for a short period of time (e.g. on the order of thirty seconds or so) to allow the patient's hemodynamics to settle into a relatively steady state. In a further embodiment, process 300 may be performed when the patient is asleep or at rest to further minimize transient effects upon the heart. Periods of sleep or rest may be identified by a clock in IMD 100, by a manual activation, by accelerometer data (e.g. accelerometer 212 in FIG. 2), or by any other technique. Likewise, process 300 may be withheld when the patient is active or extremely active, or otherwise has a high heart rate, as appropriate.

Analysis of heart rate turbulence suitably begins by identifying a perturbation to the patient's heart such as a PVC or other change the heartbeat that results in a change in the patient's hemodynamics. Various forms of cardiac perturbations may include any ventricular beat originating from a different source than a baseline beat, or that produces a smaller or larger output from the heart. Perturbations may be naturally-occurring, or may be initiated by IMD 100 as described more fully below. A perturbation may be generated, for example, by inducing a premature beat in either ventricle, and/or by adjusting the rate at which either the left and/or right ventricle are paced. In the context of baseline ventricular pacing, for example, changes in hemodynamic pressure can be induced in the patient by pacing a single ventricle for one or more beats.

In an exemplary embodiment, naturally-occurring PVCs in the patient are identified by monitoring electrocardiogram (ECG) data such as a PQRST waveform or the like within IMD 100. Data may be collected according to any scheme, but in an exemplary embodiment data measurements are taken at regular time intervals with a sufficiently high frequency to identify any natural perturbations of the patient's heart rate. Although an exemplary process 300 discussed herein emphasizes monitoring ECG data for purposes of simplicity and illustration, other equivalent data factors such as processing of atrial and ventricular EGMs and their relative timings with respect to each other and/or with respect to the previous and subsequent beats may be used in addition to or in place of ECG data in various alternate but equivalent embodiments. In a further exemplary embodiment, perturbations following unusual conditions may be ignored or differently processed by IMD 100, as discussed below, so that the patient's condition can be monitored over time under relatively constant conditions.

In an alternate embodiment, IMD 100 induces extrasystolic beats (atrial or ventricular), PVCs and/or other cardiac perturbations so that the patient's reactions can be appropriately monitored and/or tested. In such embodiments, IMD 100 suitably provides pacing to the heart prior to the premature beat to place the heart into a steady rhythmic state, as described above. Further, IMD 100 may provide a string of extrastimuli entrainment beats (e.g. S1 beats) immediately prior to the premature beat to further place the heart into a known state. In an exemplary embodiment, a train of about twenty S1 beats having a pacing rate of about ten percent above the intrinsic rate may be provided by IMD 100, followed by a premature S2 beat at about sixty percent of the S1 rate. Of course, any combination of S1, S2, S3, S4 and/or other beats at any pacing rate or prematurity could be used in alternate embodiments. Accordingly, cardiac perturbations observed within step 304 may be naturally-occurring and/or induced by IMD 100.

When a perturbation is identified, the patient's reaction to the perturbation is observed and/or recorded (step 306). The reaction may be observed by monitoring ECG or EGM data or any other data to determine the rate and magnitude of any resulting heart rate turbulence. In an exemplary embodiment, atrial contraction intervals (A—A intervals) and/or ventricular contraction intervals (V—V intervals) are monitored from the patient's ECG data for the period following the perturbation. Data may be gathered for any interval of time or for any number of beats, or for any other duration. In an exemplary embodiment, data is gathered for about twenty beats following the perturbation, or until the heart returns to its original pre-perturbed state. Data gathered is stored in memory 104 (FIG. 1) or another appropriate location for processing by IMD 100. Data gathered prior to the perturbation may also be stored within memory 104, or elsewhere on IMD 100.

In various embodiments, it may be desirable to analyze the patient's condition under relatively constant conditions over time. Variations in the perturbation may therefore create inconsistent data that may be of reduced benefit. To avoid this situation, in certain embodiments IMD monitors the patient's heart beat cycle length, coupling intervals and/or other parameters prior to the perturbation so that perturbations resulting from unusual baseline conditions may be flagged or otherwise differently processed. If a patient experiences PVCs following coupling intervals of 500 ms, 550 ms and 800 ms, for example, analysis of the 800 ms PVC may be ignored or separated from the analysis of the other PVCs in various embodiments. Accordingly, certain embodiments may ignore or otherwise differently-process perturbations that occur following unusual or non-standard conditions.

After data is gathered, the stored data is processed to quantify the heart rate turbulence experienced by the patient and to correlate the HRT to the patient's hemodynamic status. HRT may be quantified according to any process, including evaluation of turbulence onset (TO), turbulence slope (TS), turbulence timing (TT), and/or any other parameter related to changes in heart rate following a perturbation to the heart. Turbulence onset is generally considered to be the percentage difference between the heart rate immediately following the perturbation and the rate immediately preceding the perturbation. One formula for calculating turbulence onset is:

$$TO=((RR_1+RR_2)-(RR_{-2}+RR_{-1}))/(RR_{-2}+RR_{-1})*100$$

where $RR_{-2}$ and $RR_{-1}$ are the last two normal intervals preceding the perturbation, and $RR_1$ and $RR_2$ are the first two normal intervals following the perturbation. "RR" refers to the R—R interval as measured from ECG waveform data, although other parameters could be used in alternate embodiments. Alternate time-based techniques for quantifying HRT include measuring the time for the heart rate to return to a normal level following the perturbation, or measuring the time from the perturbation to the minimum or maximum R—R interval observed in a window of time following the perturbation.

Any number of parameters could be derived from the tachogram, including turbulence slope (TS) and turbulence timing (TT). The turbulence slope (TS) is generally considered to be the maximum positive slope of the linear regression line drawn through five (or so) consecutive measurement points in an averaged tachogram. Because the tachogram generally plots the time elapsed between beats, TS is generally expressed in milliseconds per beat, although other ECG intervals could alternatively be analyzed. The turbulence timing (TT) is generally the first beat number (or the time of that beat) in the sequence producing the maximum positive slope of the linear regression line drawn through five (or so) consecutive measurement points in a tachogram. TT is generally expressed as either a beat number or in milliseconds. In an exemplary embodiment, processor 102 suitably calculates the slopes of several lines using a sliding scale of five or so beats. In this manner, the slope for each line is calculated, and the maximum slope is identified as indicating the patient's HRT. If a sliding window of five beats is used across a twenty-beat pattern, for example, processor 102 suitably calculates fifteen measurements. Of course patterns or windows having any number of beats could be used in calculating the various slopes in alternate embodiments.

Heart rate turbulence may be correlated to a patient's hemodynamic condition or overall cardiac health in any manner. Generally speaking, larger values for HRT following a perturbation are considered to be more favorable than smaller values, since the greater turbulence generally indicates better baroreflexes in the patient. As discussed more fully below, HRT may be stored within IMD 100 to track changes over time. Extremely low values of HRT may provide IMD 100 to issue an alarm or warning for the patient to seek medical attention, and/or IMD 100 may use HRT to process an additional response (step 310) such as administering a drug, neurological or other therapy, or to adjust pacing rates or other parameters. Process 300 may be executed repetitively (step 312) to maintain data over time, or to iteratively adjust a therapy or other parameter. In such embodiments, therapies may be applied in a "closed loop" manner, whereby continuous monitoring of the patient's condition is provided as feedback to drive application and/or adjustment of one or more therapies. Neurostimulation or other treatments, for example, may be applied in such magnitudes and durations as appropriate to bring the patient's cardiac condition back to normal, or to improve the condition. In such embodiments, HRT or other parameters can be monitored and/or titrated in a "closed loop" manner using conventional control techniques until the parameter reaches a desired value.

Figure 4:
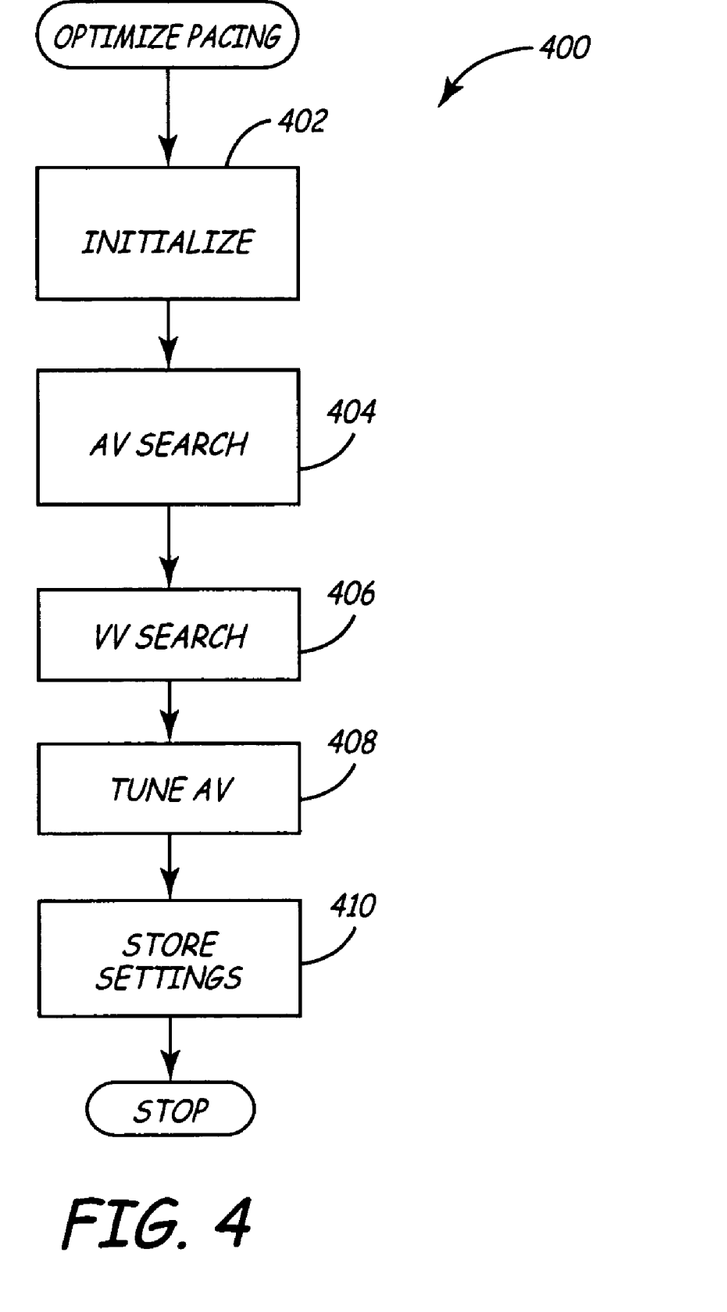
FIG. 4 is a flowchart of an exemplary process for optimizing pacing parameters as a function of heart rate turbulence.

HRT observations following a PVC or other perturbation may be used to optimize therapy parameters within a pacemaker or other implantable device 100 capable of delivering therapy. With reference now to FIG. 4, an exemplary process 400 for optimizing pacing parameters suitably includes the broad steps of setting initial pacing parameters to be evaluated (step 402), adjusting one parameter (e.g. the atrial-ventricular (A-V) interval) (step 404), adjusting a second parameter (e.g. the cross-ventricular (V—V) interval) (step 406), optionally re-visiting the first parameter (e.g. A-V interval) (step 408), and storing the optimal settings (step 410) for continued operation of IMD 100. The various steps of process 400 may be implemented with computer-executable instructions stored in a digital memory 104 and that are appropriately executed by processor 102 (FIG. 1), or by any other processor associated with IMD 100.

Initial pacing parameters (step 402) may be set to any convenient initial value as determined from statistical models, historical data, patient history, physician input or any other source. In an exemplary embodiment, initial pacing intervals may be about 100 ms for A-V interval and about 0 ms for V—V interval, although any other intervals could be used. Optimization of pacing intervals takes place using any suitable technique, such as the iterative technique described below in conjunction with FIG. 5. Generally speaking, IMD 100 gradually modifies the pacing parameters while monitoring HRT resulting from the changes. Because high HRT generally correlates to better cardiac performance, the parameter that produces the highest HRT may be deemed to be optimal for continued pacing. After an optimal parameter for one type of pacing (e.g. A-V pacing) is identified, that setting can be used during optimization of another pacing parameter. After both parameters have been optimized, various embodiments include cross-checking of the first parameter (step 408) so that the optimal pacing parameters for both types of pacing are evaluated together. Although FIG. 4 shows A-V interval evaluation (step 404) as taking place prior to V—V interval evaluation (step 406), the respective order may be altered such that V—V intervals are optimized prior to A-V intervals, with any follow-up V—V optimization taking place after an optimal A-V interval is determined.

Figure 5:
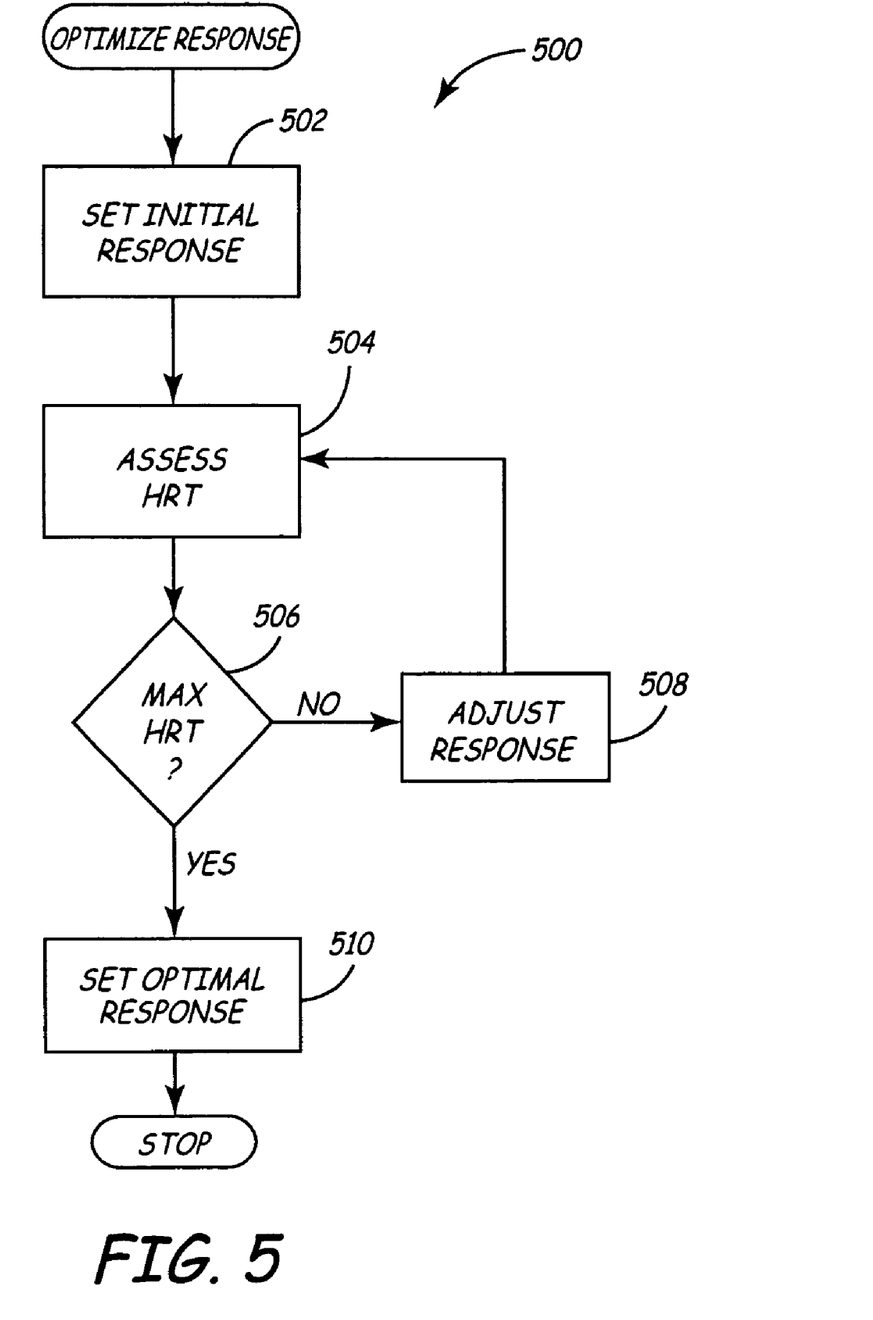
FIG. 5 is a flowchart of an exemplary process for tuning a response generated by an implanted medical device as a function of heart rate turbulence.

With reference now to FIG. 5, an exemplary process 500 for optimizing a response from an IMD 100 suitably includes iteratively providing a response (step 502), determining the heart rate turbulence produced by the response (step 504), and adjusting the response (step 508) until an optimal (e.g. a maximum) HRT is identified. Responses that may be optimized in various embodiments include pacing parameters, administration of drug or neuro-therapies, or the like. As with the processes described above, the various steps of process 500 may be implemented with computer-executable instructions stored in a digital memory 104 or other storage medium and executed by any processor 102 associated with IMD 100.

To begin the optimization process, a baseline response is initially provided from IMD 100 (step 502). Baseline responses may be obtained from historical data, patient history, physician input, or any other source. For example, to optimize A-V intervals, the baseline AV interval may be initially set at about 100 ms with no V—V delay. Once the AV interval is optimized, the V—V interval optimization may begin with an interval of about 0 ms, with the A-V interval set at the optimal level previously determined, for example, in step 404 of FIG. 4. Baseline levels of drug or neurostimulation therapy could alternatively be provided.

As the initial response from IMD 100 is applied, the patient's HRT is observed (step 504) using the techniques described above in conjunction with FIG. 3 as appropriate. HRT may be quantified using turbulence onset, turbulence slope, turbulence timing, and/or any other parameter, for example, to determine the patient's reaction to the initial therapy. After the initial response is processed, IMD 100 suitably varies the response provided (step 508) to obtain additional data points for comparison (step 506). As mentioned above, increased HRT generally correlates to improved hemodynamic condition, so process 500 generally seeks to maximize the level of HRT in the patient (step 506).

The observed value for each iteration is suitably maintained in IMD 100 for comparison against subsequent observations. In an embodiment that seeks to optimize A-V intervals, for example, HRT observations may be obtained for AV intervals of 80 ms, 100 ms, 120 ms or the like. If the maximum HRT is produced at 120 ms, further data may be collected at 130 ms or so until a maximum value is identified. If the maximum HRT is produced at 100 ms, the response may be adjusted to, say, 90 ms and/or 110 ms to isolate a maximum value. Further iterations may provide improved resolution, thus resulting in a more accurate optimal value produced. Of course other embodiments will use widely varying values, and the particular parameters used in this illustrative example are not intended to be limiting in any way.

When an optimal parameter value is identified by the iterative process (steps 504, 506 and 508 of FIG. 5), that parameter may be set (step 510) within the IMD 100 for continued application, or the value may be processed in other ways. In an equivalent embodiment of process 500, application of the response (i.e. steps 502 and 508) may be manually provided by a health care clinician or another source external to IMD 100, while monitoring functions (step 504) continue to be provided by IMD 100.

Accordingly, various methods and apparatus for diagnosing and gauging cardiac condition using heart rate turbulence are provided. While exemplary embodiments have been presented in the foregoing detailed description of the invention, it should be appreciated that a vast number of variations exist. It should also be appreciated that these exemplary embodiments are only examples, and are not intended to limit the scope, applicability, or configuration of the invention in any way. Rather, the foregoing detailed description will provide a convenient road map for implementing an exemplary embodiment of the invention. Various changes may be made in the function and arrangement of elements described in an exemplary embodiment without departing from the scope of the invention as set forth in the appended claims and their legal equivalents.

What is claimed is:

1. A method for quantifying heart rate turbulence of a patient that is automatically executable by a medical device, the method comprising the steps of:
   registering a cardiac perturbation characteristic with a sensing circuit of a medical device;
   measuring a heart rate turbulence parameter resulting from the cardiac perturbation characteristic with a measuring circuit of the medical device for at least two cardiac cycles subsequent to the registered perturbation characteristic; and
   quantifying the heart rate turbulence parameter based at least in part upon the measured heart rate turbulence parameter to determine a present hemodynamic status of a patient.

2. The method of claim 1 wherein the registering step comprises inducing the cardiac perturbation characteristic with a stimulus provided by the medical device.

3. The method of claim 2 further comprising the step of:
   determining whether or not the patient is at rest prior to performing the method.

4. The method of claim 1 wherein the cardiac perturbation characteristic is a premature ventricular contraction.

5. The method of claim 1 wherein the cardiac perturbation characteristic comprises a change in heart rate.

6. The method of claim 1 wherein the cardiac perturbation characteristic comprises a change in hemodynamic pressure.

7. The method of claim 1 wherein the quantifying step comprises identifying a maximum positive slope in a stream of heartbeat cycle lengths following the cardiac perturbation.

8. The method of claim 1 wherein the quantifying step comprises measuring an amount of time following registration of the cardiac perturbation characteristic for the patient to return to a normal heart rate.

9. The method of claim 1 wherein the quantifying step comprises measuring a period of time following registration of the cardiac perturbation characteristic until a minimum cycle length occurs.

10. The method of claim 1 further comprising the step of providing a response signal from the medical device based upon the hemodynamic status.

11. The method of claim 10 wherein the response comprises providing a medication.

12. The method of claim 10 wherein the response comprises providing an electrical signal to the heart.

13. The method of claim 10 wherein the response comprises neurological stimulation.

14. The method of claim 10 wherein the response comprises adjusting a pacing parameter.

15. The method of claim 10 wherein the response comprises storing data about the hemodynamic status in a computer readable memory unit of the medical device.

16. The method of claim 17 wherein the response comprises providing a medication.

17. The method of claim 10 further comprising the steps of gathering a feedback data about the heart as the response is provided, and adjusting the response as a function of the feedback data.

18. The method of claim 17 wherein the response comprises adjusting a pacing parameter.

19. A medical device implanted in a patient, the device comprising:
   a data collection module configured to identify a heart rate turbulence parameter in the patient following a cardiac perturbation over at least two subsequent cardiac cycles;
   a data processing module in communication with the data collection module, wherein the data processing module is configured to correlate the heart rate turbulence parameter to a hemodynamic status of the patient; and
   a response module in communication with the data processing module, wherein the response module is configured to provide a response based upon the hemodynamic status.

20. The device of claim 19 further comprising a digital memory in communication with the data processing module, and wherein the response comprises storing historical data about the hemodynamic status in the memory.

21. The device of claim 20 wherein the response module comprises an interface to at least one pacing electrode.

22. The device of claim 21 wherein the data processing module is further configured to induce the heart rate turbulence in the patient using the at least one pacing electrode.

23. The device of claim 19 wherein the data processing module is further configured to adjust the response as a function of the reaction.

24. The device of claim 23 wherein the response comprises administering a drug therapy.

25. The device of claim 23 wherein the response comprises adjusting a pacing parameter.

26. A medical device implanted in a patient, the device comprising:

means for observing a cardiac perturbation of the patient;
means for measuring a heart rate turbulence parameter resulting from the cardiac perturbation over at least two subsequent cardiac cycles; and
means for quantifying the heart rate turbulence parameter to determine a hemodynamic status of the patient.

27. The medical device of claim 26 further comprising means for inducing the cardiac perturbation in the patient from the implantable medical device.

28. The medical device of claim 26 further comprising means for providing a response from the implantable medical device based upon the hemodynamic status.

29. A method of calibrating a parameter using an implantable medical device, the method comprising the steps of:
providing a cardiac perturbation to a patient from the implantable medical device using an initial value of the parameter;
observing heart rate turbulence in the patient as a result of the cardiac perturbation;
adjusting a value of the parameter in response to the heart rate turbulence observed; and
repeating the adjusting and observing steps until a maximum amount of heart rate turbulence is observed in the patient.

30. The method of claim 29 further comprising the step of setting an optimal value for the parameter, wherein the optimal value corresponds to the value used to generate the maximum amount of heart rate turbulence.

31. The method of claim 30 wherein the parameter is a pacing interval.

32. The method of claim 31 wherein the pacing interval is an A-V pacing interval.

33. The method of claim 31 wherein the pacing interval is a V—V pacing interval.

34. The method of claim 31 wherein the cardiac perturbation comprises a change in heart rate.

35. The method of claim 31 wherein the cardiac perturbation comprises a change in hemodynamic pressure.

36. The method of claim 31 wherein the cardiac perturbation comprises a premature ventricular contraction.

37. A method of claim 31 wherein the pacing interval comprises delivery of at least one post extra-systolic stimulus resulting in increased ventricular stroke volume for at least one successive cardiac cycle.

38. A method according to claim 37, wherein the delivery of said at least one post extra-systolic stimulus occurs at least 100 ms following the end of a refractory period of the ventricle.

39. The method of claim 30 wherein the parameter is a drug therapy.

40. The method of claim 30 wherein the parameter is a neurotherapy.

* * * * *